United States Patent [19]
Edwards et al.

[11] Patent Number: 4,996,308
[45] Date of Patent: Feb. 26, 1991

[54] DERIVATIVES WITH UNSATURATED SUBSTITUTIONS FOR THE 5'-HYDROXYMETHYL GROUP

[75] Inventors: Michael L. Edwards, Cincinnati; James R. McCarthy, West Chester; Nellikunja J. Prakash, Cincinnati, all of Ohio

[73] Assignee: Merrell Dow Pharmaceuticals Inc., Cincinnati, Ohio

[21] Appl. No.: 173,782

[22] Filed: Mar. 25, 1988

[51] Int. Cl.$^5$ .................. C07H 19/167; C07H 19/173
[52] U.S. Cl. .......................................... 536/26; 536/24
[58] Field of Search ............... 536/23, 24, 26; 514/45, 514/46

[56] References Cited

U.S. PATENT DOCUMENTS 3,472,837 10/1969 Verheyden et al. ................. 536/26
3,910,885 10/1975 Moffatt et al. ...................... 536/23

FOREIGN PATENT DOCUMENTS 1113851 5/1968 United Kingdom .

OTHER PUBLICATIONS

Brimacombe, Angewandte Chemie Intl. Ed., 8(6), 401–468 (1969).
Cook et al., J. Am. Chem. Soc., 101, 1554–1564 (1979).
Jenkins et al., J. Am. Chem. Soc., 98(11), 3346–3357 (1976).
Richards et al., Carbohydrate Research, 100, 315–329 (1982).
Verheyden et al., Ann. N.Y. Acad. Sci., 255, 151–165 (1975).
Bennett et al., [Mol. Pharmacol., 29, 383 (1986)].
De Clercq, [Biochem. Pharmacol., 36, 2567–75 (1987)].
Ferrier, Advances in Carbohydrate Chemistry and Biochemistry, vol. 24, pp. 250–251 (1969).
Aarbakke et al., Cancer Res., 46, 5469 (1986).
Montgomery et al., J. Med. Chem., 25, 626 (1982).
Clercq et al., Antiviral Res., 3, 17 (1983).
Baker et al., Tetrahedron Letters, 30, 2939 (1974).
Craig et al., J. Orig. Chem., 51, 1258 (1986).
Jenkins et al., J. Amer. Chem. Soc., 98, 3346.

Primary Examiner—Johnnie R. Brown
Assistant Examiner—L. Eric Crane
Attorney, Agent, or Firm—Louis J. Wille

[57] ABSTRACT

This invention relates to certain acetylenic, cyano and allenic aristeromycin/adenosine derivatives which are useful in inhibiting AdoMet-dependent transmethylation and in the treatment of patients afflicted with neoplastic or viral disease states.

25 Claims, No Drawings

DERIVATIVES WITH UNSATURATED SUBSTITUTIONS FOR THE 5'-HYDROXYMETHYL GROUP

BACKGROUND OF THE INVENTION

S-Adenosyl-L-methionine (AdoMet) dependent transmethylation reactions have been implicated in a variety of biological processes related to viral growth and replication, viral transformation of cells, growth of malignant cells, and processes such as chemotaxis and secretion [See P. M. Ueland, Pharm. Reviews, 34, 223 (1982)]. In general, these transmethylation reactions are catalyzed by various transmethylases which utilize AdoMet as a methyl-donor substrate in the methylation of a number of methyl-acceptor substrates such as catechols; norepinephrine; histamine; serotonin; tryptamine; membrane phospholipids; lysyl, arginyl, histidyl, aspartyl, glutamyl, and carboxyl groups of certain proteins; tRNA and mRNA; and DNA. These various transmethylases produce S-Adenosine-L-Homocysteine (AdoHcy) as a byproduct upon transfer of a methyl group from AdoMet to the appropriate methyl-acceptor substrate.

AdoHcy has been shown to be a potent feed-back inhibitor of the AdoMet-dependent transmethylation reactions. This feed-back inhibition of the transmethylases is controlled by the biodegradation of AdoHcy by S-Adenosyl-L-Homocysteine Hydrolase which provides a homeostatic control on the tissue levels of AdoHcy. The activity of S-Adenosyl-L-Homocysteine Hydrolase is generally considered by those skilled in the art to play an important role in regulating the tissue levels of AdoHcy and thereby controlling the activity of the AdoMet dependent transmethylation reactions.

The compounds of the present invention are inhibitors of S-Adenosyl-L-Homocysteine Hydrolase. These compounds therefore inhibit the naturally-occurring biodegradation of AdoHcy and result in elevated tissue levels of AdoHcy. Elevated levels of AdoHcy in turn provide an endogenous feed-back inhibition of various AdoMet dependent transmethylation reactions which are associated with biological processes related to viral growth and replication, viral transformation of cells, growth of malignant cells, and processes such as chemotaxis and secretion. The compounds of the present invention are therefore useful as inhibitors of these biological processes and useful in an end use application as therapeutic agents in the treatment of patients afflicted with various pathological conditions in which these processes are implicated, such as, viral infections and neoplastic disease states.

SUMMARY OF THE INVENTION

The present invention relates to novel acetylenic, cyano and allenic aristeromycin/adenosine derivatives which are useful as inhibitors of S-Adenosyl-L-Homocysteine Hydrolase and are useful as anti-viral and anti-neoplastic agents.

The present invention provides novel compounds of the formula (1)

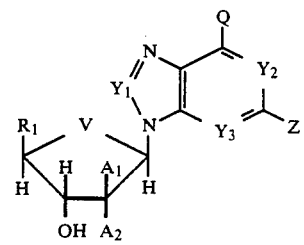

wherein
V is oxy, methylene, or thio,
$R_1$ is ethynyl or cyano,
$A_1$ and $A_2$ are each independently hydrogen, halogen, or hydroxy with the provisos that where $A_1$ is hydroxy, $A_2$ is hydrogen, and that where $A_2$ is hydroxy, $A_1$ is hydrogen,
$Y_1$ is nitrogen, a CH group, a CCl group, a CBr group or a $CNH_2$ group,
$Y_2$ and $Y_3$ are each independently nitrogen or a CH group,
Q is $NH_2$, NHOH, $NHCH_3$, or hydrogen, and
Z is hydrogen, halogen, or $NH_2$; and pharmaceutically-acceptable salts thereof.

In addition, the present invention also provides novel compounds of the formula (1a)

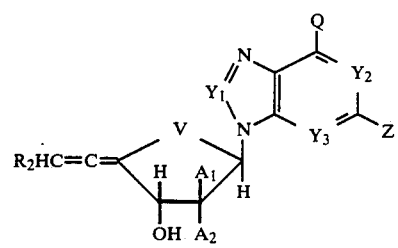

wherein
V is oxy, methylene, or thio
$R_2$ is hydrogen or $C_1$–$C_4$ alkyl,
$A_1$ and $A_2$ are each independently hydrogen, halogen, or hydroxy with the provisos that where $A_1$ is hydroxy, $A_2$ is hydrogen, and that where $A_2$ is hydroxy, $A_1$ is hydrogen,
$Y_1$ is nitrogen, a CH group, a CCl group, a CBr group or a $CNH_2$ group,
$Y_2$ and $Y_3$ are each independently nitrogen or a CH group,
Q is $NH_2$, NHOH, $NHCH_3$, or hydrogen, and
Z is hydrogen, halogen, or $NH_2$; and pharmaceutically-acceptable salts thereof.

The present invention also provides a method of inhibiting AdoMet-dependent transmethylation activity in a patient in need thereof comprising administration of an effective inhibitory amount of a compound of formula (1) or (1a).

Another embodiment of the present invention is a method of treating a patient afflicted with a neoplastic disease state or in controlling the growth of a neoplasm in a patient afflicted with a neoplastic disease state comprising administration of an effective antineoplastic dose of a compound of formula (1) or (1a).

A further embodiment of the present invention is a method of treating a patient afflicted with a viral infection or of controlling a viral infection in a patient afflicted therewith comprising administration of an effective antiviral amount of a compound of formula (1) or (1a).

DETAILED DESCRIPTION OF THE INVENTION

As used herein, the term "halogen" refers to a fluorine, chlorine, bromine, or iodine atom and the term "nitrogen" refers to a trivalent nitrogen atom attached to two radicals. The term "ethynyl" refers to a radical of the formula $-C\equiv CH$ and the term "cyano" refers to a radical of the formula $-C\equiv N$. The term "$C_1$-$C_4$ alkyl" refers to a saturated straight or branched chain hydrocarbyl radical of one to four carbon atoms.

The aristeromycin/adenosine derivatives of formula (1) or (1a) can be prepared by utilizing procedures and techniques well known and appreciated by one skilled in the art.

A general synthetic procedure for the preparation of compounds of formula (1) wherein $R_1$ is ethynyl is set forth in Scheme A. In the following schemes all substituents, unless otherwise indicated, are as previously defined.

SCHEME A

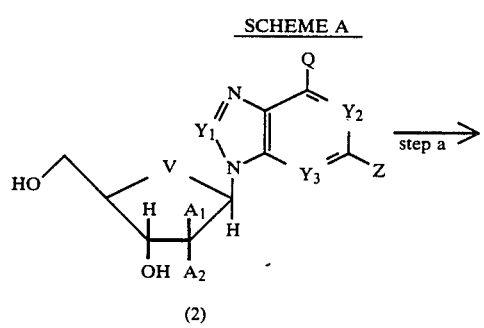

(2)

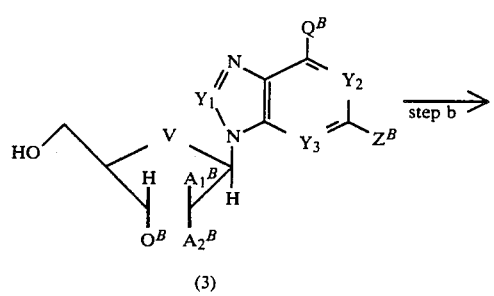

(3)

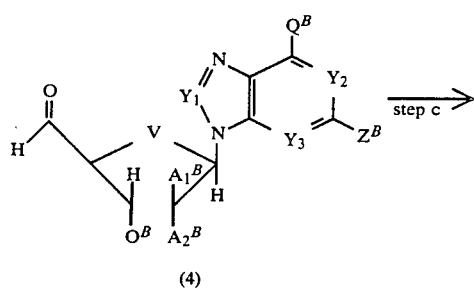

(4)

-continued
SCHEME A

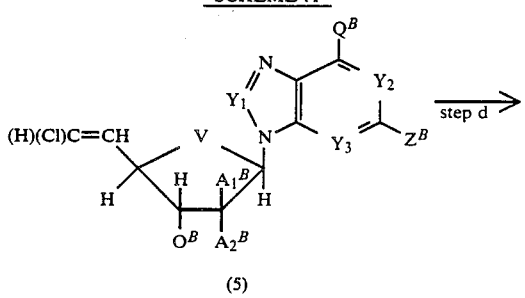

(5)

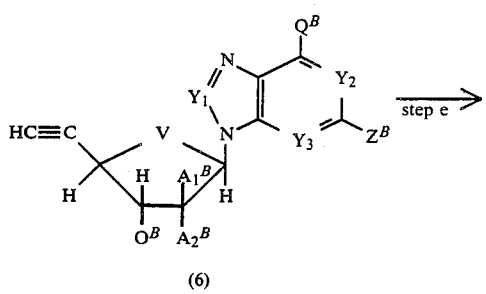

(6)

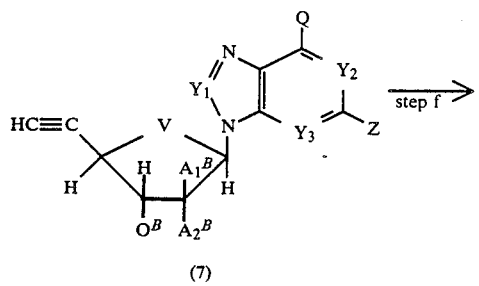

(7)

(8)

In step a, reactive hydroxy, amino, or hydroxylamino groups other than the 5'-hydroxy group of the appropriate starting material, as represented by formula (2), are blocked with standard blocking agents well known in the art. These blocking groups can be conventional amino protecting groups for Q and Z (wherein Q or Z are $NH_2$) and conventional hydroxy protecting groups for the 3'-hydroxy, for $A_1$ or $A_2$ (wherein $A_1$ or $A_2$ are OH), and for Q (wherein Q is hydroxylamino). $O^B$, $A_1^B$, $A_2^B$, $Q^B$ and $Z^B$ in Scheme A represent the 3'-hydroxy, $A_1$, $A_2$, Q, and Z groups as herein defined blocked with a blocking group where appropriate.

The selection and utilization of particular blocking groups are well known to one of ordinary skill in the art. In general, blocking groups should be selected which adequately protect the amino or hydroxy groups in question during subsequent synthetic steps and which are readily removable under conditions which will not cause degradation of the desired product.

Examples of suitable hydroxy protecting groups are $C_1$–$C_6$ alkyl, tetrahydropyranyl, methoxymethyl, methoxyethoxymethyl, t-butyl, benzyl, and triphenylmethyl. The term $C_1$–$C_6$ alkyl refers to a saturated hydrocarbyl radical of one to six carbon atoms of straight, branched, or cyclic configuration. The preferred blocking groups for the 3'-hydroxy and for $A_2$ (wherein $A_2$ is hydroxy) include 2',3'-O-isopropylidene (formed by reacting the unblocked compound with acetone) and alkoxymethyldene (formed by reacting the unblocked compound with trialkylorthoformate).

Examples of suitable amino protecting groups are benzoyl, formyl, acetyl, trifluoroacetyl, phthalyl, tosyl, benzenesulfonyl, benzyloxycarbonyl, substituted-benzyloxycarbonyl (e.g., p-chloro, p-bromo, p-nitro, p-methoxy, o-chloro, 2,4-dichloro, and 2,6-dichloro derivatives), t-butyloxycarbonyl (Boc), t-amyloxycarbonyl, isopropyloxycarbonyl, 2-(p-biphenyl)-isopropyloxycarbonyl, allyloxycarbonyl, cyclopentyloxycarbonyl, cyclohexyloxycarbonyl, adamantyloxycarbonyl, phenylthiocarbonyl, and triphenylmethyl. The preferred amino protecting group is the di-benzoyl derivative made by reacting the unblocked compound with benzoyl chloride.

In step b, the appropriately blocked 5'-hydroxy derivative (3) is oxidized to the corresponding aldehyde (4). The preferred oxidizing reagent is dicyclohexylcarbodiimide, methyl phosphonic or dichloroacetic acid and dimethylsulfoxide.

The aldehyde (4) can optionally be derivatized so as to improve the handling characteristics of the compound or to facilitate purification thereof by means of procedures and techniques well known and appreciated in the art. For example, the 5',5'-(N,N'-diphenylethylenediamino) derivative can be prepared by the method of Ranganathan et al. [J. Org. Chem., 39, 290 (1974)].

In step c, the vinyl chloride derivative (5) is formed by reacting the corresponding aldehyde (4) with chloromethyltriphenylphosphonium chloride or similar alkylating reagent. Chloromethyltriphenylphosphonium chloride is preferred.

In step d, the vinyl chloride derivative (5) is dehydrohalogenated to form the ethynyl derivative (6). The preferred reagent to effect the dehydrohalogenation is lithium diisopropylamide.

In step e, the amino-protecting groups are removed utilizing procedures and techniques well known and appreciated in the art. For example, the benzoyl amino blocking groups can be removed by hydrolysis with ammonia.

In step f, the hydroxy protecting groups are removed according to conventional procedures and techniques well known and appreciated in the art. For example, the 2',3'-O-isopropylidene blocking group can be removed by reacting (7) with aqueous trifluroacetic acid.

Starting materials for use in the general synthetic procedure outlined in Scheme A are readily available to one of ordinary skill in the art. For example, certain starting materials for various compounds of formula (1) and (1) are listed in Table 1.

TABLE 1

Examples of Starting Materials for Scheme A
Compound of formula (1) or (1a) wherein

| V | $A_1$ | $A_2$ | $Y_1$ | $Y_2$ | $Y_3$ | Z | Q | Source of Starting Material |
|---|---|---|---|---|---|---|---|---|
| O | H | OH | CH | N | CH | H | $NH_2$ | J. Med. Chem. 25, 626(1982) |
| O | OH | H | CH | N | N | H | $NH_2$ | Het. Chem. 14, 195(1977) |
| $CH_2$ | H | OH | CH | N | N | H | $NH_2$ | JACS 88, 3885 (1966) |
| O | H | H | CH | N | N | H | $NH_2$ | 2'-Deoxyadenosine(commercially available) |
| $CH_2$ | H | OH | CH | N | CH | H | $NH_2$ | J. Med. Chem. 25, 626(1982) |
| O | OH | H | CH | N | N | F | $NH_2$ | JACS 86, 1242 (1964) |
| O | H | OH | CH | CH | N | H | $NH_2$ | Nucleosides & Nucleotides, 1985, p. 625 |
| $CH_2$ | H | OH | CH | N | N | H | $NH_2$ | J. Pharm. Sci. 62, 1252(1973) |
| $CH_2$ | H | $CH_2$ | CH | N | N | $NH_2$ | $NH_2$ | J. Med. Chem. 27, 670(1984) |
| $CH_2$ | H | H | CH | N | N | H | $NH_2$ | J. Med. Chem. 27, 1416 (1984) |
| $CH_2$ | OH | H | CH | N | N | H | $NH_2$ | J. Med. Chem. 20, 612(1977) |
| $CH_2$ | H | OH | N | N | N | H | $NH_2$ | J. Het. Chem. 10, 601(1973) |
| $CH_2$ | H | H | N | N | N | $NH_2$ | $NH_2$ | J. Med. Chem. 27, 1416(1984) |
| $CH_2$ | H | H | N | N | N | H | $NH_2$ | J. Het. Chem. 10, 601(1973) |
| $CH_2$ | H | H | N | N | N | $NH_2$ | $NH_2$ | J. Med. Chem. 27, 1416(1984) |
| $CH_2$ | H | OH | N | N | N | $NH_2$ | $NH_2$ | J. Med. Chem. 27, 670(1984) |
| $CH_2$ | OH | H | N | N | N | $NH_2$ | $NH_2$ | J. Pharm. Sci. 69, 1019(1980) |
| $CH_2$ | H | OH | CH | CH | N | H | $NH_2$ | Nucleosides Nucleotides 3, 345(1984) |

TABLE 1-continued

Examples of Starting Materials for Scheme A
Compound of formula (1) or (1a) wherein

| V | $A_1$ | $A_2$ | $Y_1$ | $Y_2$ | $Y_3$ | Z | Q | Source of Starting Material |
|---|---|---|---|---|---|---|---|---|
| $CH_2$ | H | OH | CH | CH | N | H | $NHCH_3$ | JACS 85, 193 (1963) |
| $CH_2$ | H | OH | CBr | CH | N | H | $NH_2$ | JACS 86, 1242 (1964) |
| S | H | OH | CH | N | N | H | $NH_2$ | Biochemistry 9, 2367(1970) |

Additional starting materials can be prepared by the use of methods analogous to those described in Table 1 as well as other conventional methods as are well known and appreciated in the art.

The following example presents a typical synthesis as described by Scheme A. This example is understood to be illustrative only and is not intended to limit the scope of the present invention in any way.

EXAMPLE 1

9-(5',5',6',6'-Tetradehydro-5,'6'-Dideoxy-$\beta$-D-Ribo-Hexofuranosyl)-9-H-Purin-6-Amine Step a: $N^6$-benzoyl-2',3'-O-isopropylidene-adenosine.

Convert adenosine to its 2',3'-acetonide followed by benzoylation to the $N^6$-benzoyl derivative according to the procedure of Smrt et al. [Coll. Czech. Chem. Comm. 29, 224 (1964)].

Step b: $N^6,N^6$-Bis benzoyl-5'-deoxy-2',3'-O-isopropylidene-5'-,5'-(N,N'-diphenylethylenediamino)adenosine.

Convert $N^6$-benzoyl-2',3'-O-isopropylidene adenosine to $N^6$-benzoyl-5'-deoxy-2',3'-O-isopropylidene-5',5'-(N,N'-diphenylethylenediamino)adenosine according to the procedure of Ranganathan et al. [J. Org. Chem. 39, 290 (1974)]. To 2.96 g of this product in 10 ml of pyridine, cooled in an ice bath, add 1.15 ml (9.9 mmol) of benzoyl chloride. Stir the mixture overnight at room temperature and pour into ice water. Extract the product into 100 ml of chloroform and dry with magnesium sulfate. Evaporate the solution on a rotary evaporator and add toluene. Repeat the evaporation in vacuo, and collect 4.07 g of a yellow foam. Percolate the product through a 40 mm $\times$ 10 cm flash silica gel column with 4% ethyl acetate/96% dichloromethane. Combine and evaporate the appropriate fractions and collect a yellow oil. Dissolve the oil in ethanol and evaporate three times to yield a solid. Triturate the solid with 50 ml of ethanol and filter. Dry the solid in vacuo to give 2.67 g of the title compound [mp 135–138 degrees Celsius (°C.)].

NMR (CDCl$_3$, 90 MHz): $\delta$ 1.30 (3H, S) 1.50 (3H, S), 3.3–3.7 (4H, m), 4.55 (1H, m), 5.1 (2H, d, J=2), 5.65 (1H, d, J=2), 6.1 (1H, S), 6.3–7.8 21H, M), 8.40 (1H, S).

Step b continued:
$N^6,N^6$-Bisbenzoyl-2',3'-O-isopropylidene adenosine-5'-aldehyde.

To 2.64 g (3.73 mmol) of $N^6,N^6$-Bis-benzoyl-5'-deoxy-2',3'-O-isopropylidene-5',5'-(N,N'-diphenylethylenediamino)adenosine in 370 ml of dichloromethane at 0° C. add a solution of 1.56 g (8.2 mmol) p-toluenesulfonic acid monohydrate in 180 ml of acetone. Stir the mixture for 1.5 hours and filter. Evaporate the filtrate on a rotary evaporator and partition the residue between 200 ml of dichloromethane and water. Dry the dichloromethane solution with magnesium sulfate and evaporate to a foam. Dissolve 2.10 g of the foam in 200 ml of benzene and reflux in a Dean-Stark apparatus for one hour. Evaporate the solvent to give 2.06 g of the title compound. (NMR Spectrum reveals more than 80% of the product as aldehyde.)

NMR (CDCl$_3$, 90 MHz): $\delta$ 1.40 (3H, S) 1.70 (3H, S), 4.65 (1H, S), 5.3 (1H, d, J=7), 5.45 (1H, broad d, J=7), 6.2 (1H, S), 7.2–7.8 (10H, m), 8.10 (1H, S), 8.45 (major) and 8.55 (1H together, two S). 9.3 (1H, S, CHO).

Step c:
$N^6,N^6$-Bis-benzoyl-2',3'-O-isopropylidene-9-(6'-chloro-5',6'-dideoxy-$\beta$-D-ribohex-5'-enofuranosyl)-9-H-purin-6-amine.

To a solution of lithium diisopropylamide (20 mmol) in 500 ml tetrahydrofuran (THF) which has been chilled to $-30°$ C., add chloromethyltriphenylphosphonium chloride (6.8 g, 20 mmol). Allow the mixture to warm to 0° C. and hold at this temperature for 1 hr. Chill the solution to $-70°$ C. and add in a dropwise manner a solution of the $N^6,N^6$-bis-benzoyl-2',3'-O-isopropylideneadenosine-5'-aldehyde (6.5 g, 13 mmol) in THF (100 ml). Stir the reaction mixture at $-70°$ C. for 2 hr and thereafter pour the mixture into water/dichloromethane. Separate the organic layer, dry with anhydrous magnesium sulfate, and evaporate to dryness. Chromatograph the residue on a silica gel flash column eluting with hexane/ethyl acetate (1.5/1) to yield the title compound (4.1 g) as a white foam.

MS: (CI) MH+ =546.

Anal: Calc'd for $C_{28}H_{24}ClN_5O_5.\frac{1}{3}CH_3C(O)OC_2H_5$: C 61.14, H 4.68, N 12.17.

Found: C 61.35, H 4.62, N 12.25.

Step d:
$N^6,N^6$-Bisbenzoyl-9-(5',5',6',6'-tetradehydro-5',6'-dideoxy-2',3'-O-isopropylidene-$\beta$-D-ribo-hexofuranosyl)-9-H-purin-6-amine To a solution of lithium diisopropylamide (8 mmol) in 120 ml THF which has been chilled to $-70°$ C., add in a dropwise manner a solution of $N^6,N^6$-Bis-benzoyl-2',3'-O-isopropylidene-9-(6-chloro-5,6-dideoxy-$\beta$-D-ribohex-5-enofuranosyl)-9-H-purin-6-amine in 15 ml of THF. Stir the reaction mixture at $-70°$ C. for 2 hr. Pour the mixture into water and extract the aqueous mixture with dichloromethane. Combine the organic extracts, dry over anhydrous MgSO$_4$, and evaporate the organic solvent to dryness. Chromatograph the residue on a silica gel flash column eluting with hexane/ethyl acetate (2/1) to yield the title compound (0.8 g) as a foam.

MS: (CI) MH+ =510.

Step e:
9-(5′,5′,6′,6′-Tetradehydro-5′,6′-dideoxy-2′,3′-O-isopropylidene-β-D-ribo-hexofuranosyl]-9-H-purin-6-amine Stir a mixture of $N^6,N^6$-Bisbenzoyl-9-(5′,5′,6′,6′-tetradehydro-5′,6′-dideoxy-2′,3′-0-isopropylidene-β-D-ribo-hexofuranosyl)-9-H-purin-6-amine (800 mg, 1.6 mmol) in 10 ml of methanol and 10 ml of concentrated aqueous ammonia overnight at ambient temperature. Evaporate the mixture and chromatograph the residue on a silica gel flash column eluting with ethyl acetate. Recrystallize the purified title compound from hexane/ethyl acetate to yield a white solid (170 mg) with a melting point of 210°–211° C.

Anal: Calc'd for $C_{14}H_{15}N_5O_5$: C 55.81, H 5.02, N 23.24.
Found: C 55.65, H 5.03, N 22.98.
MS: (CI) $MH^+ = 302$.

Step f:
9-(5′,5′,6′,6′-Tetradehydro-5′,6′-dideoxy-β-D-ribo-hexofuranosyl)-9-H-purin-6-amine Heat a solution of 9-(5′,5′,6′,6′-Tetradehydro-5′,6′-dideoxy-2′,3′-O-isopropylidene-β-D-ribo-hexofuranosyl)-9-H-purin-6-amine (270 mg) in water/formic acid (30 ml each) in a 50° C. oil bath under a nitrogen atmosphere for 2 hr. Evaporate the mixture and recrystallize the residue from methanol to yield the title compound (122 mg) as a white solid with a melting point of 213°–214° C.

Anal: Calc'd for $C_{11}H_{11}N_5O_3 \cdot 3/4\ H_2O$: C 48.08, H 4.58, N 25.49.
Found: C 48.43, H 4.52, N 25.12.
MS: (CI) $MH^+ = 262$.

The following specific compounds can be made by procedures analogous to those described above in Example 1:

3-(5′,5′,6′,6′-Tetradehydro-5′,6′-dideoxy-β-D-ribofuranosyl)-3H-1,2,3-triazolo[4,5-d]pyrimidin-7-amine 1-(5′,5′,6′,6′-Tetradehydro-5′,6′-dideoxy-β-D-ribofuranosyl)-1H-imidazo[4,5-c]pyridin-4-amine 9-(5′,5′,6′,6′-Tetradehydro-5′,6′-dideoxy-4-thio-β-D-ribo-hexofuranosyl)-9H-purin-6-amine 9-(5′,5′,6′,6′-Tetradehydro-5′,6′-dideoxy-β-D-arabinohexofuranosyl)-9H-purin-6-amine 1R-(1.alpha.,2.alpha.,3.beta.,5.beta.)-3-(9H-purin-6-amine-9-yl)-5-ethynyl-1,2-cyclopentanediol The aristeromycin/adenosine derivatives of the formula (1) wherein $R_1$ is cyano can be prepared according to conventional procedures and techniques well known and appreciated by one of ordinary skill in the art. A general synthetic procedure is set forth in Scheme B.

SCHEME B

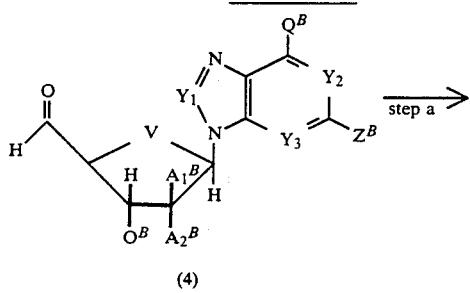

(4)

-continued
SCHEME B

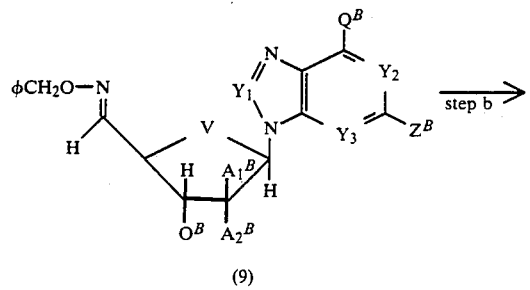

(9)

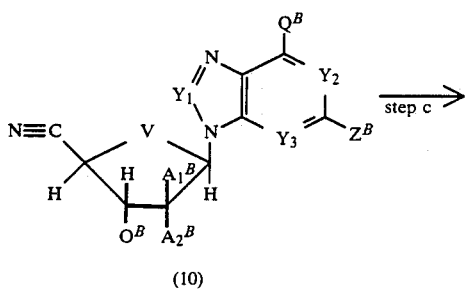

(10)

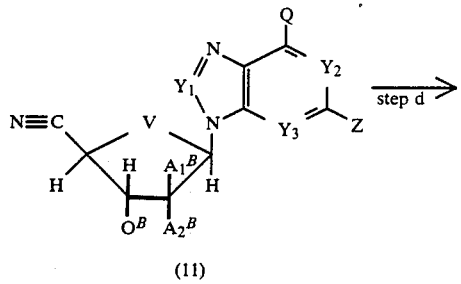

(11)

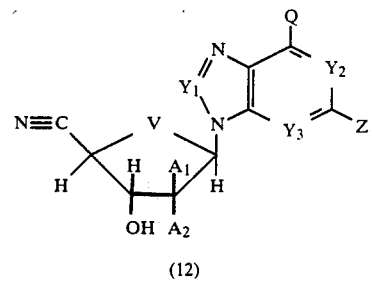

(12)

In step a, the aldehyde derivative (4) in which the appropriate amino and hydroxy groups have been blocked in a manner analogous to that described in Scheme A is converted to the corresponding oxime derivative (9). The preferred reagent for this reaction is O-benzylhydroxylamine which results in the O-benzyloxime being formed. The aldehyde derivative (4) can alternatively be converted to the free oxime by reaction with hydroxylamine hydrochloride.

The oxime derivative (9) is then converted to the cyano derivative (10) in step b by reaction with an appropriate base such as lithium diisopropylamide. Where the free oxime is used, the preferred reagent is tosyl chloride in an appropriate base.

In steps c and d, the amino and hydroxy blocking groups can then be removed in a manner analogous to that described in Scheme A (steps e and f).

Alternatively, the aristeromycin/adenosine derivatives of formula (1) wherein $R_1$ is cyano can be prepared by converting the appropriate 5'-acid or corresponding ester [wherein the reactive hydroxy, amino, or hydroxylamino groups are blocked as described in Scheme A (step a)] to the 5'-carboxamide by procedures well known and appreciated in the art. This 5'-carboxamide can then be dehydrated to the desired nitrile by use of a variety of reagents such as, for example, phosphorus pentoxide, phosphoryl chloride/pyridine or trichloromethyl chloroformate. The blocking groups can then be removed as described in Scheme A (steps e and f).

The following example presents a typical synthesis as described by Scheme B. This example is understood to be illustrative only and is not intended to limit the scope of the present invention in any way.

EXAMPLE 2

9-($\beta$-D-Ribofuranylnitrile)-9-H-Purin-6-Amine

Step a:
$N^6,N^6$-Bisbenzoyl-5'-deoxy-2',3'-O-isopropylideneadenosine-5'-carboxaldehyde-O-benzyloxime Prepare $N^6,N^6$-bisbenzoyl-2',3'-O-isopropylidene adenosine-5'-aldehyde as described in Example 1. Combine the adenosine aldehyde derivative (2.6 g, 3.7 mmol) and O-benzylhydroxylamine (0.85 g, 4 mmol) in 50 ml ethanol and heat at 60° C. in an oil bath until the reaction is complete. Evaporate the reaction mixture and chromatograph the residue on a flash silica gel column eluting with ethyl acetate/hexane to yield the title compound as a foam.

Step b:
$N^6,N^6$-Bisbenzoyl-9-(2',3'-O-isopropylidene-$\beta$-D-ribofuranylnitrile)-9-H-purin-6-amine Add $N^6,N^6$-bisbenzoyl-5'-deoxy-2',3'-O-isopropylideneadenosine-5'-carboxaldehyde-O-benzyloxime (618 mg, 1 mmol) to a solution of lithium diisopropylamide (2 mmol) in THF (25 ml) which is chilled to −70C. Stir the reaction mixture at −70° C. until the reaction is complete as indicated by thin layer chromatography. Pour the mixture into water/dichloromethane and allow the layers to separate. Dry the organic layer over anhydrous magnesium sulfate and evaporate to dryness. Chromatograph the residue on a flash silica gel column eluting with ethyl acetate/hexane to yield the title compound as a foam.

Steps c and d:
9-($\beta$-D-Ribofuranylnitrile)-9-H-purin-6-amine

Sequentially de-block the $N^6,N^6$-Bisbenzoyl-9-(2',3'-O-isopropylidene-$\beta$-D-ribofuranylnitrile)-9-H-purin-6-amine as described in steps e and f of Example 1 to yield the title compound. Recrystallize the product from methanol.

The following specific compounds can be made by procedures analogous to those described above in Example 2:
9-($\beta$-D-arabinofuranonitrile)-9H-purin-6-amine
9-(4-thio-$\beta$-D-ribofuranonitrile)-9H-purin-6-amine
1R-(1.alpha., 2.alpha., 3.beta., 5.beta.)-3-(9H-purin-6-amine-9-yl)-5-cyano-1,2-cyclopentanediol
1-($\beta$-D-ribofuranonitrile)-1H-imidazo[4,5-c]pyridin-4-amine The allenic aristeromycin/adenosine derivatives of the formula (1a) can be prepared according to conventional procedures and techniques well known in the art.

A general synthetic procedure for the preparation of compounds of formula (1a) is set forth in Scheme C.

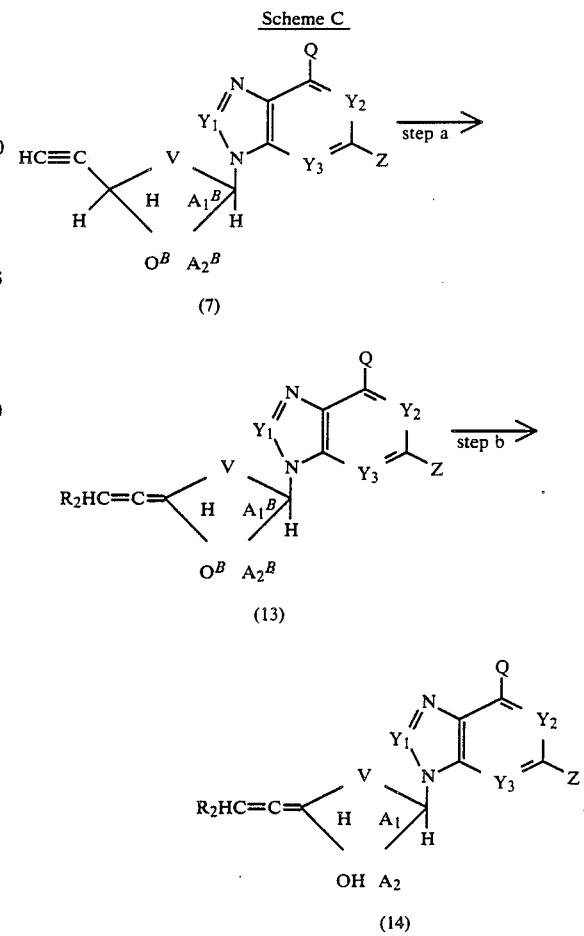

In step a, the partially de-blocked acetylenic derivative (7), which is prepared according to the procedures outlined in Scheme A and bears blocking groups on any reactive hydroxy moieties, is isomerized with base to provide the desired allenic derivative (13). Where a compound of formula (1a) is desired wherein $R_2$ is hydrogen, the acetylenic derivative can be reacted with sodium ethoxide. Where a compound of formula (1a) is desired wherein $R_2$ is alkyl, the acetylenic derivative (7) can be treated with base such as lithium diisopropylamide, and reacted with the appropriate $C_1$–$C_4$ alkyl halide according to procedures well known and appreciated in the art. This results in the formation of the appropriately alkylated acetylenic derivative which can then be further reacted as described above in steps (a) and (b).

In step b, the amino blocking groups can then be removed in a manner analogous to that described in Scheme A (step f).

The following example presents a typical synthesis as described by Scheme C. This example is understood to be illustrative only and is not intended to limit the scope of the present invention in any way.

EXAMPLE 3

9-(4',5',5',6'-Tetradehydro-5',6'-Dideoxy-β-D-Ribo-hexofuranosyl)-9-H-Purin-6-Amine

Step a:
9-(4',5',5',6'-tetradehydro-5',6'-dideoxy-2',3'-O-isopropylidene-β-D-ribo-hexofuranosyl)-9H-purin-6-amine Prepare 9-(5',5',6',6'-tetradehydro-5',6'-dideoxy-2',3'-O-isopropylidene-β-D-ribo-hexofuranosyl)-9-H-purin-6-amine as described in Example 1. Add the partially blocked acetylenic derivative (600 mg) to a solution of sodium ethoxide in ethanol which has been prepared by dissolving 100 mg of sodium metal in 20 ml of ethanol. Reflux the reaction mixture for 1 hr under a nitrogen atmosphere. Cool the mixture, pour into water/dichloromethane, and allow the organic phase to separate. Dry the organic layer over anhydrous magnesium sulfate and evaporate to dryness. Recrystallize from a mixture of hexane/dichloromethane/methanol to yield the title compound (230 mg) as a white powder with a melting point of 209° C. (shrinks 182° C.).

MS: (CI) MH+ = 302.

Anal: Calc'd for $C_{14}H_{15}N_5O_3$: C 55.81, H 5.02, N 23.24.

Found: C 55.36, H 5.03, N 23.46.

NMR ($^{13}C$): shows central allene C at 196.25 ppm.

In like manner, 9-(4',5',5',6'-tetradehydro-5',6', dideoxy-2',3'-O-ethoxymethylidene-β-D-ribo-hexofuranosyl)-9-H-purin-6-amine can be prepared from 9-(4',5',5',6'-tetradehydro-5',6'dideoxy-2',3'-O-ethoxymethylidene-β-D-ribo-hexofuranosyl)-9-H-purin-6amine which is prepared by reacting the appropriate starting material with triethylorthoformate in trichloroacetic acid and following the procedures set forth in Scheme A.

Step b:
9-(4',5',5',6'-tetradehydro-5',6'-dideoxy-β-D-ribo-hexofuranosyl)-9-H-purin 6-amine Add 9-(4',5',5',6'-tetradehydro-5',6'-dideoxy-2',3'-O-isopropylidene-β-D-ribo-hexofuranosyl)-9-H-purin-6-amine (50 mg) and $PdCl_2(CH_3CN)_2$ (5 mg) to aqueous acetonitrile (5 ml) and stir until the reaction is complete. Evaporate the reaction mixture and recrystallize the product from methanol to yield the title compound as a white solid.

Where the 2',3'-O-ethoxymethylidene derivative is employed, stir a solution of 9-(4',5',5',6'-tetradehydro-5',6'-dideoxy-2',3'-O-ethoxymethylidene-β-D-ribohexofuranosyl)-9-H-purin-6-amine (50 mg) and pyridinium p-toluenesulfonate (50 mg) in ethanol (12 ml) and $H_2O$ (6 ml) at 40° C. until the ethoxymethylidene protecting groups are cleaved. Evaporate the reaction mixture and recrystallize the product from methanol.

The following specific compounds can be made by procedures analogous to those described above in Example 3:

1R-(1.alpha., 2.alpha, 3.beta.)-3-(9H-purin-6-amine-9-yl)-5-propadienyl-1,2-cyclopentanediol
3-(4',5',5',6'-tetradehydro-5',6'-dideoxy-β-D-ribohexofuranosyl)-3H-imidazo[4,5-b]pyridin-7-amine
3-(4',5',5',6'-tetradehydro-5',6'-dideoxy-4'-thio-β-D-ribohexofuranosyl)-3H-imidazo[4,5-b]pyridin-7-amine
9-(4',5',5',6'-tetradehydro-5',6'-dideoxy-4'-thio-β-D-ribohexofuranosyl)-9H-purin-6-amine An alternative procedure for preparing acetylenic, cyano and allenic adenosine derivatives of the formula (1) or (1a) is set forth in Scheme D. This method involves preparing the adenosyl base and ribosyl moieties separately and then effecting a condensation of the moieties.

SCHEME D

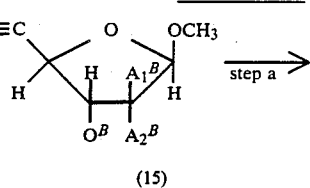

(15)

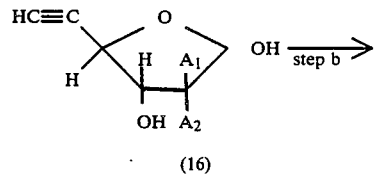

(16)

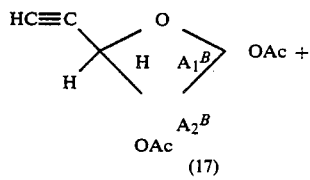

(17)

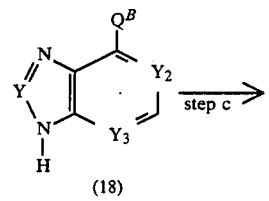

(18)

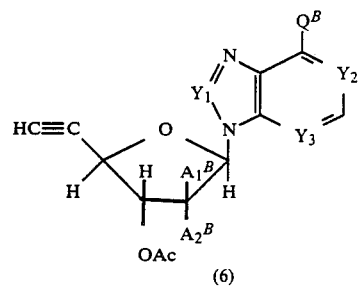

(6)

Acetylenic ribosyl derivatives (15) are prepared according to standard techniques and procedures which are well known and appreciated by those of ordinary skill in the art. For example, these compounds can be prepared from the appropriate ribosyl derivatives by methods analogous to those described in Scheme A. Appropriate stating materials are readily available.

These derivatives (15) are hydrolyzed in step a using an acid such as acetic acid. The hydrolyzed derivatives (16) are subsequently converted to the corresponding acetic acid esters (17) in step b by reaction with acetic anhydride in pyridine.

Procedures for making the adenine derivative (18) also involve standard techniques and procedures which are well known and appreciated by those of ordinary skill in the art.

The acetic acid ester (17) can be condensed with the appropriate adenine derivative (18) through a fusion reaction or through a condensation reaction in the presence of bis-trimethylsilylacetamide and a Lewis acid such as trimethylsilyltrifluoromethanesulfonate.

The condensed product (6) can then be de-blocked by hydrolysis as described in Scheme A (steps e and f) or further reacted to provide compounds of formula (1a) as described in Scheme C.

Compounds of formula (1) wherein $R_1$ is cyano can also be prepared according to methods analogous to those described in Scheme D.

Starting materials for use in the general synthetic procedure outlined in Scheme C are readily available to one of ordinary skill in the art. For example, the starting materials for various compounds of formula (1) or (1a) are listed in Table 2.

TABLE 2

Examples of Starting Materials for Scheme D
Compound of formula (1) or (1a) wherein

| V | $A_1$ | $A_2$ | $Y_1$ | $Y_2$ | $Y_3$ | Z | Q | Source of Starting Material |
|---|---|---|---|---|---|---|---|---|
| O | H | OH | CH | N | N | Cl | $NH_2$ | 2-Chloroadenine and Tet. Lett. 1977,3433 |
| O | H | OH | CH | N | N | H | $NH_2$ | Adenine |
| $CH_2$ | H | OH | CH | N | CH | H | $NH_2$ | 3-deazaadenine |

Additional starting materials can be prepared by the use of methods analogous to those described in Table 2 as well as other conventional methods as are well known and appreciated in the art.

In another embodiment, the present invention provides a method of inhibiting AdoMet-dependent transmethylation activity in a patient in need thereof which comprises administration of a compound of the formula (1) or (1a) in an effective inhibitory amount. The term "effective inhibitory amount" refers to an amount sufficient to inhibit the AdoMet-dependent transmethylation activity after single or multiple dose administration.

As used herein, the term "patient" refers to a warm-blooded animal such as a mammal which is afflicted with a particular disease state. It is understood that dogs, cats, rats, mice, horses, bovine cattle, sheep, and humans are examples of animals within the scope of the meaning of the term.

The compounds of formula (1) or (1a) are believed to exert their inhibitory effect on AdoMet-dependent transmethylation by inhibition of AdoHcy Hydrolase thereby providing an increase in tissue levels of AdoHcy which in turn provides feedback inhibition of AdoMet-dependent transmethylation. However, it is understood that the present invention is not limited by any particular theory or proposed mechanism to explain its effectiveness in an end-use application.

As is well known and appreciated by those skilled in the art, various disease states, such as certain neoplastic disease states and viral infections, are characterized by excessive AdoMet-dependent transmethylation activity. As used herein, the term "excessive" means a level of activity which allows the disease state to progress.

More specifically, the present invention provides a method for the treatment of a patient afflicted with a neoplastic disease state which is characterized by excessive AdoMet dependent transmethylation activity comprising the administration of an effective antineoplastic amount of a compound of formula (1) or (1a). The term "neoplastic disease state" as used herein refers to an abnormal state or condition characterized by rapidly proliferating cell growth or neoplasm. Neoplastic disease states which are characterized by an excessive AdoMet-dependent transmethylation activity and for which treatment with a compound of formula (1) or (1a) will be particularly useful include: Leukemias such as, but not limited to, acute lymphoblastic, chronic lymphocytic, acute myloblastic and chronic mylocytic; Carcinomas, such as, but not limited to, those of the cervix, oesophagus, stomach, small intestines, colon and lungs; Sarcomas, such as, but not limited to, oesteoma, osteosarcoma, lipoma, liposarcoma, hemangioma and hemangiosarcoma; Melanomas, including amelanotic and melanotic; and mixed types of neoplasias such as, but not limited to carcinosarcoma, lymphoid tissue type, folicullar reticulum, cell sarcoma and Hodgkins Disease.

An effective antineoplastic amount of a compound of formula (1) or (1a) refers to an amount which is effective, upon single or multiple dose administration to the patient, in controlling the growth of the neoplasm or in prolonging the survivability of the patient beyond that expected in the absence of such treatment. As used herein, "controlling the growth" of the neoplasm refers to slowing, interrupting, arresting or stopping its growth and metastases and does not necessarily indicate a total elimination of the neoplasm.

In addition, the present invention provides a method for the treatment of a patient afflicted with a viral infection which is characterized by excessive AdoMet-dependent transmethylation activity comprising the administration of an effective antiviral amount of a compound of formula (1) or (1a). The term "viral infection" as used herein refers to an abnormal state or condition characterized by viral transformation of cells, viral replication and proliferation. Viral infections which are characterized by an excessive AdoMet dependent transmethylation activity and for which treatment with a compound of formula (1) or (1a) will be particularly useful include: Retroviruses such as, but not limited to, HTLV-I, HTLV-II, human immunodeficiency viruses, HTLV-III (AIDS virus), and the like; RNA viruses such as, but not. limited to, influenza type A, B, and C, mumps, measles, rhinovirus, dengue, rubella, rabies, hepatitis virus A, encephalitis virus, and the like; DNA viruses such as, but not limited to, herpes, vaccinia, pappiloma virus (wart), hepatitis virus B, and the like.

An effective antiviral amount of a compound of formula (1) or (1a) refers to an amount which is effective in controlling the virus. This viral control refers to slowing, interrupting, arresting or stopping the viral transformation of cells or the replication and proliferation of the virus and does not necessarily indicate a total elimination of the virus.

An effective dose can be readily determined by the attending diagnostician, as one skilled in the art, by the use of conventional techniques and by observing results obtained under analogous circumstances. In determining the effective dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

Effective antineoplastic and antiviral amounts of a compound of formula (1) or (1a) are expected to vary from about 0.1 milligram per kilogram of body weight per day (mg/kg/day) to about 100 mg/kg/day. Preferred amounts are expected to vary from about 0.5 to about 10 mg/kg/day.

In an additional embodiment, the present invention relates to a method of treating a patient afflicted with a neoplastic disease state or a viral infection comprising administration of an effective antineoplastic or antiviral amount of a compound of formula (1) or (1a) wherein Q is $NH_2$ in conjunctive therapy with an effective inhibitory amount of an Adenosine Deaminase (ADA) inhibitor. The term "conjunctive therapy" contemplates coadministration of (1) or (1a) along with an ADA inhibitor at essentially the same time, or treatment of the patient with an ADA inhibitor prior to or after treatment with a compound of formula (1) or (1a). An effective inhibitory amount of an ADA inhibitor is an amount effective in significantly inhibiting ADA in the patient.

ADA deaminates compounds of formula (1) or (1a) wherein Q is $NH_2$ and thereby degrades the active compounds to relatively inactive metabolites. When a compound of formula (1) or (1a) wherein Q is $NH_2$ and an ADA inhibitor are administered in conjunctive therapy, the dose will be less in amount or frequency of administration than that required when the compound of formula (1) or (1a) is administered alone.

Various pharmaceutically acceptable non-toxic ADA inhibitors can be used including, but not limited to, deoxycoformycin. An effective inhibitory amount of the ADA inhibitor will vary from about 0.05 mg/kg/day to about 0.5 mg/kg/day and preferably will be from about 0.1 mg/kg/day to about 0.3 mg/kg/day. Deoxycoformycin is the preferred ADA inhibitor for use in conjunctive therapy with compounds of formula (1) or (1a) wherein Q is $NH_2$.

In effecting treatment of a patient afflicted with a disease state described above, a compound of formula (1) or (1a) can be administered in any form or mode which makes the compound bioavailable in effective amounts, including oral and parenteral routes. For example, compounds of formula (1) or (1a) can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. In addition, compounds of formula (1) or (1a) wherein Q is $NH_2$ can be administered as above in further combination with an ADA inhibitor. The compounds of the invention, while effective themselves, may be formulated and administered in the form of their pharmaceutically acceptable acid addition salts for purposes of stability, convenience of crystallization, increased solubility and the like.

In another embodiment, the present invention provides a pharmaceutical composition comprising an effective amount of a compound of formula (1) or (1a) in admixture or otherwise in association with one or more pharmaceutically acceptable carriers or excipients. In addition, the present invention provides a pharmaceutical composition comprising an effective amount of a compound of formula (1) or (1a) wherein Q is $NH_2$ and an effective ADA inhibitory amount of an ADA inhibitor in admixture or otherwise in association with one or more pharmaceutically acceptable carriers or excipients. The term "effective amounts" as applied to compounds of formula (1) or (1a) refers to effective inhibitory, antineoplastic, or antiviral amounts as appropriate.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, such as intramuscular, intravenous, and subcutaneous, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Any of the above described pharmaceutical compositions containing compounds of formula (1) or (1a) wherein Q is NH$_2$ may also contain an effective inhibitory amount of an ADA inhibitor in admixture or otherwise in association with the above described ingredients.

As with any group of structurally related compounds which posses a particular generic utility, certain groups and configurations are preferred for compounds of formula (1) or (1a) in their end-use application.

With respect to the substituent R$_1$, compounds wherein R$_1$ is ethynyl or cyano are generally preferred. With respect to the substituent R$_2$, compounds wherein R$_2$ is hydrogen are generally preferred.

With respect to the substituents A$_1$ and A$_2$, compounds wherein one of A$_1$ and A$_2$ is hydroxy and the other is hydrogen are generally preferred. Compounds wherein A$_1$ is hydrogen and A$_2$ is hydroxy are especially preferred.

The following are additional preferred embodiments: compounds of formula (1) wherein V is oxy, compounds of formula (1a) wherein V is methylene or thio, compounds of formula (1) or (1a) wherein Y$_1$ is a CH group, compounds of formula (1) or (1a) wherein Y$_2$ is nitrogen, compounds of formula (1) or (1a) wherein Y$_3$ is nitrogen and compounds of formula (1) or (1a) wherein Z is hydrogen. Finally, with respect to Q, those compounds of formula (1) or (1a) wherein Q is NH$_2$ or NHCH$_3$ are generally preferred with those wherein Q is NH$_2$ being especially preferred.

The following list identifies compounds of the formula (1) and (1a) which are particularly preferred embodiments of the present invention:
9-(5',5',6',6'-Tetradehydro-5',6'-dideoxy-β-D-ribo-hexofuranosyl)-9H-purin-6-amine
9-(4',5',6',6'-Tetradehydro-5',6'-dideoxy-β-D-ribo-hexofuranosyl)-9H-purin-6-amine
9-(β-D-ribofuranonitrile)-9H-purin-6-amine
9-(β-D-arabinofuranonitrile)-9H-purin-6-amine
9-(4',5',5',6'-Tetradehydro-5',6'-dideoxy-4'-thio-β-D-ribohexofuranosyl)-9H-purin-6-amine The above list is intended to be merely illustrative of particularly preferred embodiments of the present invention and it is understood that the list does not limit the scope of the invention in any way.

We claim:
1. A compound of the formula

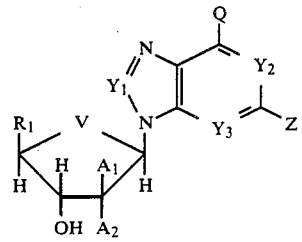

wherein
V is oxy,
R$_1$ is ethynyl or cyano,
A$_1$ and A$_2$ are each independently hydrogen or hydroxy with the provisos that where A$_1$ is hydroxy, A$_2$ is hydrogen, and that where A$_2$ is hydroxy, A$_1$ is hydrogen,
Y$_1$ is nitrogen or a CH group,
Y$_2$ and Y$_3$ are each independently nitrogen or a CH group,
Q is NH$_2$ or NHCH$_3$, and
Z is hydrogen;
and pharmaceutically-acceptable salts thereof.

2. A compound of the formula

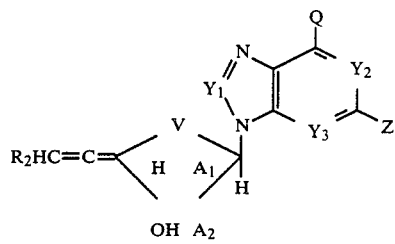

wherein
V is oxy
R$_2$ is hydrogen or C$_1$–C$_4$ alkyl,
A$_1$ and A$_2$ are each independently hydrogen or hydroxy with the provisos that where A$_1$ is hydroxy, A$_2$ is hydrogen, and that where A$_2$ is hydroxy, A$_1$ is hydrogen,
Y$_1$ is nitrogen or a CH group,
Y$_2$ and Y$_3$ are each independently nitrogen or a CH group,
Q is NH$_2$ or NHCH$_3$, and
Z is hydrogen;
and pharmaceutically-acceptable salts thereof.

3. A compound of claim 1 wherein R$_1$ is ethynyl.
4. A compound of claim 1 wherein R$_1$ is cyano.
5. A compound of claim 1 wherein V is oxy.
6. A compound of claim 2 wherein R$_2$ is hydrogen.
7. A compound of claim 1 or 2 wherein A$_2$ is hydroxy.
8. A compound of claim 1 or 2 wherein A$_1$ is hydroxy.
9. A compound of claim 1 or 2 wherein Y$_1$ is a CH group.
10. A compound of claim 1 or 2 wherein Y$_2$ is nitrogen.
11. A compound of claim 1 or 2 wherein Y$_3$ is nitrogen.
12. A compound of claim 1 or 2 wherein Z is hydrogen.

13. A compound of claim 1 wherein the compound is 9-(5',5',6',6'-tetradehydro-5',6'-dideoxy-β-D-ribo-hexofuranosyl)-9-H-purin-6-amine.

14. The compound of claim 1 wherein the compound is 9-(β-D-ribofuranonitrile)-9H-purin-6-amine.

15. The compound of claim 1 wherein the compound is 9-(β-D-arabinofuranonitrile)-9H-purin-6-amine.

16. The compound of claim 1 wherein the compound is 3-(5',5',6',6'-tetradehydro-5',6'-dideoxy-β-D-ribofuranosyl)-3H-1,2,3-triazolo[4,5-d]pyrimidin-7-amine.

17. The compound of claim 1 wherein the compound is 1-(5',5',6',6'-tetradehydro-5',6'-dideoxy-β-D-ribofuranosyl)-1H-imidazo[4,5-c]pyridin-4-amine.

18. The compound of claim 1 wherein the compound is 9-(5',5',6',6'-tetradehydro-5',6'-dideoxy-4-thio-β-D-ribo-hexofuranosyl)-9H-purin-6-amine.

19. The compound of claim 1 wherein the compound is 9(5',5', 6',6'-tetradehydro-5',6'-dideoxy-β-D-arabinohexofuranosyl)-9H-purin-6-amine.

20. The compound of claim 1 wherein the compound is 9-(4-thio-β-D-ribofuranonitrile)-9H-purin-6-amine.

21. The compound of claim 1 wherein the compound is 1-(β-D-ribofuranonitrile)-1H-imidazo[4,5-c]pyridin-4-amine.

22. The compound of claim 2 wherein the compound is 3-(4',5',5',6'-tetradehydro-5',6'-dideoxy-β-D-ribohexofuranosyl)-3H-imidazo[4,5-b]pyridin-7-amine.

23. The compound of claim 2 wherein the compound is 3-(4',5',5',6'-tetradehydro-5',6'-dideoxy-4'-thio-β-D-ribohexofuranosyl)-3H-imidazo[4,5-b]pyridin-7-amine.

24. The compound of claim 2 wherein the compound is 9-(4',5',5',6'-tetradehydro-5',6'-dideoxy-4'-thio-β-D-ribohexofuranosyl)-9H-purin-6-amine.

25. The compound of claim 2 wherein the compound is 9-(4',5',5',6'-tetradehydro-5',6'-dideoxy-8-D-ribohexofuranosyl)-9H-purin-6-amine.

* * * * *

UNITED STATES PATENT AND TRADEMARK OFFICE
CERTIFICATE OF CORRECTION

PATENT NO. : 4,996,308
DATED : February 26, 1991
INVENTOR(S) : Michael L. Edwards, et al.

It is certified that error appears in the above-identified patent and that said Letters Patent is hereby corrected as shown below:

At Column 6, line 30, the patent reads "(1)" and should read --(1a)--.

Signed and Sealed this

Twenty-sixth Day of January, 1993

Attest:

STEPHEN G. KUNIN

*Attesting Officer*          *Acting Commissioner of Patents and Trademarks*